(12) United States Patent
Strebelle et al.

(10) Patent No.: US 8,058,490 B2
(45) Date of Patent: *Nov. 15, 2011

(54) PROCESS FOR THE MANUFACTURE OF 1,2-DICHLOROETHANE

(75) Inventors: Michel Strebelle, Brussels (BE); Dominique Balthasart, Brussels (BE)

(73) Assignee: Solvay (Societé Anonyme), Brussels (BE)

( * ) Notice: Subject to any disclaimer, the term of this patent is extended or adjusted under 35 U.S.C. 154(b) by 335 days.

This patent is subject to a terminal disclaimer.

(21) Appl. No.: 12/304,329

(22) PCT Filed: Jun. 22, 2007

(86) PCT No.: PCT/EP2007/056268
§ 371 (c)(1),
(2), (4) Date: Dec. 11, 2008

(87) PCT Pub. No.: WO2008/000705
PCT Pub. Date: Jan. 3, 2008

(65) Prior Publication Data
US 2009/0270568 A1    Oct. 29, 2009

(30) Foreign Application Priority Data
Jun. 26, 2006 (FR) .................................... 06 05716

(51) Int. Cl.
C07C 17/15 (2006.01)
C07C 17/10 (2006.01)
(52) U.S. Cl. .................. 570/223; 570/224; 570/230
(58) Field of Classification Search .............. 570/223, 570/224, 230
See application file for complete search history.

(56) References Cited

U.S. PATENT DOCUMENTS

| | | |
|---|---|---|
| 4,910,354 A | 3/1990 | Derleth et al. |
| 5,260,247 A | 11/1993 | Helmut et al. |
| 5,527,754 A | 6/1996 | Derleth et al. |
| 6,803,342 B1 | 10/2004 | Derleth et al. |
| 7,667,084 B2 | 2/2010 | Strebelle et al. |
| 2004/0267063 A1 | 12/2004 | Harth et al. |
| 2008/0108856 A1 | 5/2008 | Strebelle et al. |
| 2008/0207966 A1 | 8/2008 | Balthasart et al. |
| 2008/0207967 A1 | 8/2008 | Strebelle et al. |
| 2008/0207968 A1 | 8/2008 | Strebelle et al. |
| 2009/0203854 A1 | 8/2009 | Strebelle et al. |
| 2009/0270579 A1 | 10/2009 | Balthasart et al. |
| 2009/0326179 A1 | 12/2009 | Balthasart et al. |

FOREIGN PATENT DOCUMENTS

| | | |
|---|---|---|
| EP | 0255156 A1 | 2/1988 |
| EP | 0494474 A1 | 7/1992 |
| EP | 0657212 A1 | 6/1995 |
| EP | 0657213 A1 | 6/1995 |
| NL | 6901398 | 11/1969 |
| WO | WO0026164 A1 | 5/2000 |
| WO | WO03048088 A1 | 6/2003 |
| WO | WO2006/067188 A1 | 6/2006 |
| WO | WO2006/067190 A1 | 6/2006 |
| WO | WO2006/067191 A1 | 6/2006 |
| WO | WO2006/067192 A1 | 6/2006 |
| WO | WO2007/147870 A1 | 12/2007 |
| WO | WO2008/000693 A1 | 1/2008 |
| WO | WO2008/000702 A1 | 1/2008 |
| WO | WO2008/107468 A1 | 9/2008 |
| WO | WO2009/106479 A1 | 9/2009 |
| WO | WO2009/147076 A1 | 12/2009 |
| WO | WO2009/147083 A1 | 12/2009 |
| WO | WO2009/147100 A1 | 12/2009 |
| WO | WO2009/147101 A1 | 12/2009 |

OTHER PUBLICATIONS

PCT International Search Report dated Aug. 30, 2007 for International Application No. PCT/EP2007/056268 (2 p.).
U.S. Appl. No. 12/919,101, filed Aug. 24, 2010, Petitjean et al.
U.S. Appl. No. 12/995,486, filed Dec. 1, 2010, Lempereur et al.
U.S. Appl. No. 12/995,518, filed Dec. 1, 2010, Petitjean et al.
U.S. Appl. No. 12/995,539, filed Dec. 1, 2010, Lempereur et al.
U.S. Appl. No. 12/995,509, filed Dec. 1, 2010, Kotter et al.

*Primary Examiner* — Jafar Parsa
(74) *Attorney, Agent, or Firm* — Beatrice C. Ortego

(57) ABSTRACT

Process for the manufacture of 1,2-dichloroethane (DCE) starting from a stream of ethane which is subjected to a catalytic oxydehydrogenation (ODH) thus producing a gas mixture containing ethylene which is then dried and conveyed to a chlorination reactor supplied with a flow of chlorine so that at least 10% of the ethylene is converted to DCE. The stream of products derived from the chlorination reactor is then conveyed to an oxychlorination reactor in which the majority of the balance of ethylene is converted to DCE.

22 Claims, 2 Drawing Sheets

PROCESS FOR THE MANUFACTURE OF 1,2-DICHLOROETHANE

CROSS-REFERENCE TO RELATED APPLICATIONS

The present application is a U.S. national stage application under 35 U.S.C. §371 of International Application No. PCT/EP2007/056268, filed Jun. 22, 2007, which claims benefit of French patent applications FR 06.05716 filed on Jun. 26, 2006, all of these applications being herein incorporated by reference in their entirety for all purposes.

TECHNICAL FIELD OF THE INVENTION

The present invention relates to a process for the manufacture of 1,2-dichloroethane (DCE), a process for the manufacture of vinyl chloride (VC) and a process for the manufacture of polyvinyl chloride (PVC).

BACKGROUND OF THE INVENTION

DCE is usually prepared by oxychlorination of ethylene using hydrogen chloride (HCl) and a source of oxygen or by direct chlorination of ethylene using chlorine. The dehydrochlorination of DCE by pyrolysis thus results in the production of VC with release of HCl. The oxychlorination and chlorination are generally carried out in parallel and the HCl produced in the pyrolysis is used in the oxychlorination.

To date, ethylene which is more than 99.8% pure is normally used for the manufacture of DCE. This very high purity ethylene is obtained via the thermal cracking of various petroleum products, followed by numerous complex and expensive separation operations in order to isolate the ethylene from the other products of the cracking and to obtain a product of very high purity.

Given the high cost linked to the production of ethylene of such high purity, and also the advantage that there could be in envisaging a process for the manufacture of VC by DCE in favourable regions that lack accessible ethylene capacities, various processes for the manufacture of DCE using ethylene having a purity of less than 99.8% have been envisaged. These processes have the advantage of reducing the costs by simplifying the course of separating the products resulting from cracking of petroleum products and by thus abandoning complex separations which are of no benefit for the manufacture of DCE.

Thus, various processes for the manufacture of DCE starting from ethylene having a purity of less than 99.8% produced by simplified cracking of ethane have been envisaged.

For example, Patent Application WO 00/26164 describes a process for the manufacture of DCE by chlorination of ethylene obtained by simplified cracking of ethane, the chlorination taking place in the presence of impurities obtained during the cracking of ethane without any other purification.

Patent Application WO 03/48088 itself describes a process for the manufacture of DCE by dehydrogenation of ethane giving rise to the formation of a fraction comprising ethane, ethylene and impurities including hydrogen, which fraction is then subjected to a chlorination and/or oxychlorination.

These processes have the disadvantage that the ethylene obtained cannot be used for a combined ethylene chlorination/oxychlorination process given that the ethylene contains impurities whose presence during the oxychlorination reaction could cause operating problems, namely poisoning of the catalyst by the heavy products and an uneconomic conversion of the hydrogen present. This hydrogen conversion would consume high-purity oxygen which would thus be sacrificed for an undesired reaction and would release a high heat of reaction during the conversion of hydrogen to water. This conversion would then limit the capability of the oxychlorination reactor, generally linked to the heat exchange capability. An unusually high investment must therefore be expended in order to guarantee the heat exchange area, and thereby the reactor volume, caused by the presence of hydrogen in the mixture.

The option taken of burning the hydrogen in a separate reactor, described in Application WO 03/48088, does not resolve the difficulty because it requires a large amount of oxygen, a stoichiometric amount relative to hydrogen, and also a large surface area for exchange to eliminate this heat of combustion. Consequently it has a significant ethylene consumption and it may have problems linked to safety. Finally, the removal of the water formed leads to an increase in the production costs.

Processes in which VC is obtained by oxychlorination of ethane and not of ethylene are also known. Such processes have not found an industrial application up till now given that as they are conducted at high temperatures, they result in a mediocre selectivity with loss of the reactants used and costs for separating and destroying the by-products and they are also characterized by problems of behaviour of the materials in a corrosive oxychlorination medium. Finally, problems linked to the behaviour of the catalysts used owing to the gradual vaporization of their constituents and also linked to the deposition of these constituents on the cold surface of the exchanger bundle are usually encountered.

SUMMARY OF THE INVENTION

One object of the present invention itself is to provide a process using ethylene having a purity of less than 99.8% which has the advantage of reducing the costs linked to the production of ethylene of higher purity and which has the advantage of avoiding the abovementioned problems.

To this effect, the invention relates to a process for the manufacture of DCE starting from a stream of ethane according to which:

a) the stream of ethane is subjected to a catalytic oxydehydrogenation producing a gas mixture containing ethylene, unconverted ethane, water and secondary constituents;

b) said gas mixture is optionally washed and dried thus producing a dry gas mixture;

c) after an optional additional purification step, the dry gas mixture is then conveyed to a chlorination reactor supplied with a flow of chlorine so that at least 10% of the ethylene is converted to 1,2-dichloroethane;

d) the 1,2-dichloroethane formed in the chlorination reactor is optionally isolated from the stream of products derived from the chlorination reactor;

e) the stream of products derived from the chlorination reactor, from which the 1,2-dichloroethane has optionally been extracted, is conveyed to an oxychlorination reactor in which the majority of the balance of ethylene is converted to 1,2-dichloroethane, after optionally having subjected the latter to an absorption/desorption step e'), during which the 1,2-dichloroethane formed in the chlorination reactor is optionally extracted if it has not previously been extracted;

f) the 1,2-dichloroethane formed in the oxychlorination reactor is isolated from the stream of products derived from the oxychlorination reactor and is optionally added to the 1,2-dichloroethane formed in the chlorination reactor;

g) the stream of products derived from the oxychlorination reactor, from which the 1,2-dichloroethane has been extracted, optionally containing an additional stream of ethane previously introduced in one of steps b) to f), is optionally recycled to step a) after having been optionally purged of gases and/or after an optional additional treatment in order to eliminate the chlorinated products contained therein.

BRIEF DESCRIPTION OF THE DRAWINGS

For a detailed description of the invention, reference will now be made to the accompanying drawings in which.

DETAILED DESCRIPTION OF PREFERRED EMBODIMENTS

Figure 1:
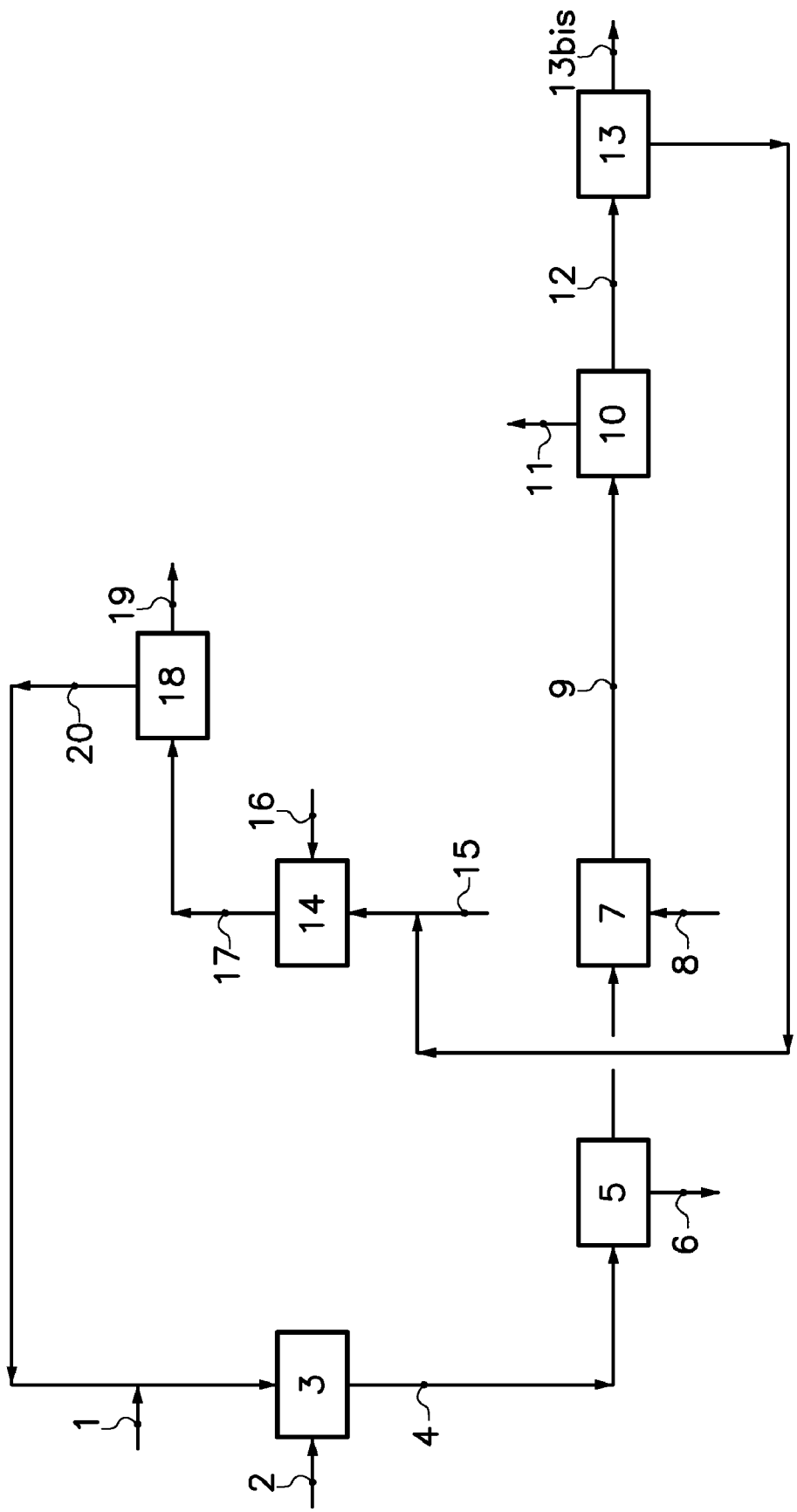
FIG. 1 illustrates a first embodiment of the process for the manufacture of DCE according to the invention.

According to step a) of the process according to the invention, the stream of ethane is subjected to a catalytic oxydehydrogenation producing a gas mixture containing ethylene, unconverted ethane, water and secondary constituents.

The stream of ethane subjected to the catalytic oxydehydrogenation may or may not be chemically pure. The stream of ethane used may contain up to 70 vol % of other gases such as methane, hydrogen, ethylene, oxygen, nitrogen and carbon oxides.

The stream of ethane used advantageously contains at least 80 vol %, preferably at least 90 vol %, particularly preferably at least 95 vol % and more particularly preferably at least 98 vol % of ethane. If necessary, the ethane may be separated from the secondary compounds having a higher boiling point in any known device, for example by absorption, extraction, diffusion or distillation.

The stream of ethane subjected to the catalytic oxydehydrogenation may be a source of ethane such as is available on the market but also the stream of products derived from the oxychlorination reactor, from which the 1,2-dichloro-ethane has been extracted, optionally containing an additional stream of ethane added to one of steps b) to f) and recycled in step g), or a mixture of the two.

The term "catalytic oxydehydrogenation (ODH)", also known as catalytic oxidative dehydrogenation, is understood to mean a partial oxidation of ethane by oxygen in the presence of a catalyst.

ODH may take place either at a temperature above 650° C. up to 800° C., below the range of thermal cracking temperatures, or at a temperature less than or equal to 650° C.

The pressure at which step a) is carried out is advantageously at least 1, preferably at least 1.5 and particularly preferably at least 2 bar absolute. It is advantageously at most 16, preferably at most 11 and particularly preferably at most 6 bar absolute.

The oxygen introduced may be oxygen or a gas containing oxygen with other inert gases, such as for example air. Preferably, oxygen is used. The oxygen may or may not be chemically pure. Thus, it is possible to use a very pure source of oxygen containing at least 99 vol % of oxygen but also a source of oxygen containing less than 99 vol % of oxygen. In the latter case, the oxygen used advantageously contains more than 90 vol % and preferably more than 95 vol % of oxygen. A source of oxygen containing from 95 to 99 vol % of oxygen is particularly preferred.

The amount of oxygen introduced, based on the amount of ethane, is advantageously from 0.001 to 1 mol/mol, preferably from 0.005 to 0.5 mol/mol and particularly preferably from 0.05 to 0.3 mol/mol.

ODH may be carried out in any known device. Advantageously, ODH is carried out in one reactor or a series of reactors of fixed bed type having one or more beds, between which a thermal conditioning step may be carried out, or in one reactor or a series of reactors of fluid bed type, preferably adiabatic or with temperature control using an auxiliary fluid inside the reactor (multitubular reactor or heat exchanger immersed in the catalytic bed) or outside the reactor. The reactants may be previously mixed before introduction into the reaction zone. One or more reactants may also be added differently, for example between the beds of a multi-bed reactor. The reactor may be equipped with preheating means and with any means necessary to control the reaction temperature. A cross exchanger advantageously enables the heat of the products formed to be recovered to reheat the incoming products.

Various catalytic systems may be used to carry out ODH according to the invention.

Thus, mention may be made of catalysts based on alkaline-earth oxides, such as for example Li/MgO catalysts generally operating at temperatures above 600° C. Mention may also be made of catalysts based on nickel (Ni). Catalysts containing molybdenum (Mo) and/or vanadium (V) have a particular advantage. These catalysts are generally based on oxides of these elements. They advantageously contain, in addition, other elements such as, for example Cr, Mn, Nb, Ta, Te, Ti, P, Sb, Bi, Zr, Ni, Ce, Al, Ca or W.

Catalysts based on vanadium (V) are more particularly advantageous.

Mixed oxides containing V and at least one other element chosen from Mo, W, Nb, Ta, Te, Ti, P, Sb, Bi, Zr, Ni, Ce, Al and Ca are preferred.

Mixed oxides containing both Mo and V, W and V or Mo, W and V are particularly preferred.

Among those containing Mo and V, mention may be made of Mo—V—O, Mo—V—Zr—O, Mo—V—Ta—Sb—Zr—O, Mo—V—Ta—Sb—O, Mo—V—Nb—Te—O, Mo—V—Nb—Bi—Ni—O, Mo—V—Nb—Bi—O, Mo—V—Nb—Ni—O, Mo—V—Nb—Sb—Ca—O, Mo—V—Ta—Al—O, Mo—V—Ta—O, Mo—V—Al—O, Mo—V—Sb—O, Mo—V—Nb—O and Mo—V—Nb—Sb.

Among those containing W and V, mention may be made of W—V—O, W—V—Nb—O, and W—V—Ta—O.

Among those containing Mo, W and V, mention may be made of Mo—W—V—Ta—Te—Ti—P—Ni—Ce—O, Mo—W—V—Ta—Te—Ti—P—O, Mo—W—V—Te—Ti—P—Ce—O, Mo—W—V—Te—Ti—P—Ni—O, Mo—W—V—Te—Ti—P—O, Mo—W—V—Te—Ti—O, Mo—W—V—Te—P—O, Mo—W—V—Te—O, Mo—W—V—Ta—Te—Ti—P—Ni—Ce—O, Mo—W—V—Ta—Te—Ti—P—O, Mo—W—V—Te—Ti—P—Ce—O, Mo—W—V—Te—Ti—P—Ni—O, Mo—W—V—Te—Ti—O, Mo—W—V—Te—P—O, Mo—W—V—Te—O, Mo—W—V—Nb—O, Mo—W—V—Sb—O, Mo—W—V—Ti—Sb—Bi—O, Mo—W—V—Ti—Sb—O, Mo—W—V—Sb—Bi—O, Mo—W—V—Zr—O, Mo—W—V—Nb—Ta—O, Mo—W—V—Nb—O and Mo—W—V—O.

Ta—Ni—O, Nb—Ni—O and Nb—Ta—Ni—O catalysts could also be used.

The catalysts used for ODH may or may not be supported. In the case where they are supported, the support which may possibly be used includes silica, alumina, titanium oxide, silicon carbide, zirconia and mixtures thereof such as mixed oxides.

The catalysts used for ODH are advantageously resistant to DCE.

The catalyst used may be placed on a bed or in tubes or outside of those tubes so that a temperature control may be obtained by a fluid surrounding these tubes or running through them.

ODH of the stream of ethane gives a gas mixture containing ethylene, unconverted ethane, water and secondary constituents. The secondary constituents may be carbon monoxide, carbon dioxide, hydrogen, various oxygen-containing compounds such as, for example, acetic acid or aldehydes, nitrogen, methane, oxygen, optionally acetylene and optionally organic compounds comprising at least 3 carbon atoms.

According to a first variant of the process according to the invention, ODH takes place at a temperature above 650° C. up to 800° C.

According to a second variant of the process according to the invention, ODH takes place at a temperature less than or equal to 650° C.

Advantageously, ODH then takes place at a temperature less than or equal to 600° C., preferably less than or equal to 550° C., particularly preferably less than or equal to 500° C., more particularly preferably less than or equal to 450° C. and most particularly preferably less than or equal to 400° C. A temperature between 200 and 400° C. is particularly advantageous.

In this case, the process according to the invention has the advantage of generating very small amounts of hydrogen responsible for many drawbacks.

According to this second variant, advantageously ODH makes it impossible to generate heavy compounds having a number of carbon atoms greater than or equal to 3, such as for example propylene and olefins whose molecular weight is higher than that of propylene, in troublesome amounts.

The second variant of the process according to the invention is preferred to the first.

According to step b) of the process according to the invention, said gas mixture obtained in step a) is optionally washed and it is dried thus producing a dry gas mixture.

The gas mixture obtained in step a) may or may not be washed. Preferably, it is washed. Washing of the gas mixture obtained in step a) may be carried out by any known means. Preferably, it is carried out using an aqueous, preferably alkaline, washing liquid, or using a non-aqueous liquid. Among the aqueous washing liquids, mention may be made of sodium hydroxide, sodium carbonate, sodium hydrogencarbonate and sodium hydroxide. Among the non-aqueous liquids, mention may be made of methylpyrrolidone, heavy oils and methanol. By this operation, solids such as coal, sulfur compounds, carbon dioxide, saturated or unsaturated hydrocarbons that are heavier than ethylene, acetylene, acid species such as acetic acid or hydrogen chloride, and aldehydes are advantageously removed.

Drying of the gas mixture may then be carried out by any known means. Preferably, drying is carried out by cooling at the end of a compression of the gases and/or by adsorption on a solid desiccant such as a molecular sieve, alumina or lime.

The washing step, when it takes place, and the drying step may take place in any order. Thus, it is possible to wash and then dry the gas mixture or to dry it and then wash it. Preferably, said gas mixture obtained in step a) is washed then it is dried, thus producing a dry gas mixture.

After step b), the amount of water in the dry gas mixture is advantageously less than or equal to 500 ppm, preferably less than or equal to 10 ppm and particularly preferably less than or equal to 1 ppm by volume.

An additional purification step, preferably a chemical purification step, of the dry gas mixture may be envisaged before it enters into the chlorination reactor in order to remove any compound that is not desired in the chlorination. This may be the case for acetylene, for example, formed during step a) but also for oxygen which is undesired when in excess.

The acetylene may advantageously be removed via a hydrogenation, preferably by means of the hydrogen present in the mixture.

According to step c) of the process according to the invention, after the aforementioned optional additional purification step, the dry gas mixture is conveyed to a chlorination reactor supplied with a flow of chlorine so that at least 10% of the ethylene is converted to DCE.

The flow of chlorine is such that at least 10%, preferably at least 20% and particularly preferably at least 40% of the ethylene is converted to DCE. The flow of chlorine is such that advantageously at most 90%, preferably at most 80% and particularly preferably at most 60% of the ethylene is converted to DCE.

According to the process of the invention, the dry gas mixture, before entering into the chlorination reactor, is advantageously characterized by an ethane content that is greater than or equal to 5%, preferably greater than or equal to 10%, particularly preferably greater than or equal to 20% and more particularly preferably greater than or equal to 25% by volume relative to the total volume of the dry gas mixture.

The dry gas mixture, before entering into the chlorination reactor, is advantageously characterized by an ethane content that is less than or equal to 95%, preferably less than or equal to 90%, and particularly preferably less than or equal to 80% by volume relative to the total volume of the dry gas mixture.

The relative ethane content is preferably greater than or equal to 10%, preferably greater than or equal to 15% and particularly preferably greater than or equal to 20% by volume of compounds other than ethylene.

The relative ethane content is preferably less than or equal to 90%, preferably less than or equal to 85% and particularly preferably less than or equal to 80% by volume of compounds other than ethylene.

The dry gas mixture, before entering into the chlorination reactor, is advantageously characterized by an ethylene content that is greater than or equal to 1%, preferably greater than or equal to 3%, and particularly preferably greater than or equal to 5% by volume relative to the total volume of the dry gas mixture.

The dry gas mixture, before entering into the chlorination reactor, is advantageously characterized by an ethylene content that is less than or equal to 50%, preferably less than or equal to 25%, by volume relative to the total volume of the dry gas mixture.

The dry gas mixture, before entering into the chlorination reactor, is advantageously characterized by a carbon monoxide content that is less than or equal to 20%, preferably less than or equal to 15%, and particularly preferably less than or equal to 10% by volume relative to the total volume of the dry gas mixture.

The dry gas mixture, before entering into the chlorination reactor, is advantageously characterized by a carbon dioxide content that is less than or equal to 30%, preferably less than or equal to 25%, and particularly preferably less than or equal to 20% by volume relative to the total volume of the dry gas mixture.

The dry gas mixture, before entering into the chlorination reactor, is advantageously characterized by an oxygen content that is less than or equal to 10%, preferably less than or equal to 5%, and particularly preferably less than or equal to 3% by volume relative to the total volume of the dry gas mixture.

The dry gas mixture, before entering into the chlorination reactor, is advantageously characterized by a nitrogen content that is less than or equal to 30%, preferably less than or equal to 15%, and particularly preferably less than or equal to 10% by volume relative to the total volume of the dry gas mixture.

The dry gas mixture, before entering into the chlorination reactor, is advantageously characterized by a hydrogen content that is less than or equal to 50%, preferably less than or equal to 35%, and particularly preferably less than or equal to 25% by volume relative to the total volume of the dry gas mixture. The chlorination reaction is advantageously carried out in a liquid phase (preferably mainly DCE) containing a dissolved catalyst such as $FeCl_3$ or another Lewis acid. It is possible to advantageously combine this catalyst with cocatalysts such as alkali metal chlorides. A pair which has given good results is the complex of $FeCl_3$ with LiCl (lithium tetrachloroferrate—as described in Patent Application NL 6901398).

The amounts of $FeCl_3$ advantageously used are around 1 to 30 g of $FeCl_3$ per kg of liquid stock. The molar ratio of $FeCl_3$ to LiCl is advantageously around 0.5 to 2.

In addition, the chlorination process is preferably performed in a chlorinated organic liquid medium. More preferably, this chlorinated organic liquid medium, also called liquid stock, is mainly composed of DCE.

The chlorination process according to the invention is advantageously carried out at temperatures between 30 and 150° C. Good results have been obtained regardless of the pressure both at a temperature below the boiling point (chlorination under subcooled conditions) and at the boiling point itself (chlorination on boiling).

When the chlorination process according to the invention is a chlorination process under subcooled conditions, it gave good results by operating at a temperature which was advantageously greater than or equal to 50° C. and preferably greater than or equal to 60° C., but advantageously less than or equal to 80° C. and preferably less than or equal to 70° C., and with a pressure in the gas phase advantageously greater than or equal to 1 and preferably greater than or equal to 1.1 bar absolute, but advantageously less than or equal to 30, preferably less than or equal to 25 and particularly preferably less than or equal to 20 bar absolute.

A process for chlorination at boiling point is particularly preferred, which makes it possible, where appropriate, to usefully recover the heat of reaction. In this case, the reaction advantageously takes place at a temperature greater than or equal to 60° C., preferably greater than or equal to 70° C. and particularly preferably greater than or equal to 85° C., but advantageously less than or equal to 150° C. and preferably less than or equal to 135° C., and with a pressure in the gas phase advantageously greater than or equal to 0.2, preferably greater than or equal to 0.5, particularly preferably greater than or equal to 1.1 and more particularly preferably greater than or equal to 1.3 bar absolute, but advantageously less than or equal to 20 and preferably less than or equal to 15 bar absolute.

The chlorination process may also be a hybrid loop-cooled process for chlorination at boiling point. The expression "hybrid loop-cooled process for chlorination at boiling point" is understood to mean a process in which cooling of the reaction medium is carried out, for example by means of an exchanger immersed in the reaction medium or by a loop circulating in an exchanger, while producing in the gaseous phase at least the amount of DCE formed. Advantageously, the reaction temperature and pressure are adjusted for the DCE produced to exit in the gas phase and for the remainder of the heat from the reaction medium to be removed by means of the exchange surface.

The dry gas mixture containing the ethylene and also the chlorine (itself pure or diluted) may be introduced, together or separately, into the reaction medium by any known device. A separate introduction of the dry gas mixture may be advantageous in order to increase its partial pressure and to facilitate its dissolution which often constitutes a limiting step of the process.

The chlorinated products obtained mainly contain DCE and also small amounts of by-products such as 1,1,2-trichloroethane or small amounts of ethane or methane chlorination products.

According to step d) of the process according to the invention, the DCE formed in the chlorination reactor is optionally isolated from the stream of products derived from the chlorination reactor. In certain cases it may be advantageous not to isolate the DCE formed in the chlorination reactor from the stream of products derived from the chlorination reactor. Preferably however, the DCE formed in the chlorination reactor is isolated from the stream of products derived from the chlorination reactor.

When it takes place, the separation of the DCE obtained from the stream of products derived from the chlorination reactor is carried out according to known methods and in general makes it possible to exploit the heat of the chlorination reaction. It is then preferably carried out by condensation and gas/liquid separation.

According to step e) of the process according to the invention, the stream of products derived from the chlorination reactor, from which the DCE has optionally been extracted, is conveyed to an oxychlorination reactor in which the majority of the balance of ethylene is converted to DCE, after optionally having subjected the latter to an absorption/desorption step e'), during which the 1,2-dichloroethane formed in the chlorination reactor is optionally extracted if it has not previously been extracted.

According to the process of the invention, the stream of products derived from the chlorination reactor, from which the DCE has optionally been extracted, before entering into the oxychlorination reactor, after the optional step e'), is advantageously characterized by an ethane content that is greater than or equal to 5%, preferably greater than or equal to 25%, by volume relative to the total volume of said stream.

The stream of products derived from the chlorination reactor, from which the DCE has optionally been extracted, before entering into the oxychlorination reactor, is advantageously characterized by an ethane content that is less than or equal to 95%, preferably less than or equal to 90%, particularly preferably less than or equal to 85% and more particularly preferably less than or equal to 80% by volume relative to the total volume of said stream.

Said stream of products, before entering into the oxychlorination reactor, is advantageously characterized by an ethylene content that is greater than or equal to 1%, preferably greater than or equal to 2%, by volume relative to the total volume of said stream.

Said stream, before entering into the oxychlorination reactor, is advantageously characterized by an ethylene content that is less than or equal to 50%, preferably less than or equal to 25%, by volume relative to the total volume of said stream.

Said stream, before entering into the oxychlorination reactor, is advantageously characterized by a content of carbon dioxide, carbon monoxide and nitrogen that is less than or equal to 70%, preferably less than or equal to 60%, and particularly preferably less than or equal to 55% by volume relative to the total volume of said stream.

Said stream, before entering into the oxychlorination reactor, is advantageously characterized by an oxygen content that is less than or equal to 10%, preferably less than or equal to 5%, and particularly preferably less than or equal to 3% by volume relative to the total volume of said stream.

Said stream, before entering into the oxychlorination reactor, is advantageously characterized by a hydrogen content that is less than or equal to 10%, preferably less than or equal to 5%, particularly preferably less than or equal to 3.5% and more particularly preferably less than or equal to 2.5% by volume relative to the total volume of said stream.

The oxychlorination reaction is advantageously carried out in the presence of a catalyst comprising active elements, including copper, deposited on an inert support. The inert support is advantageously chosen from alumina, silica gels, mixed oxides, clays and other supports of natural origin. Alumina constitutes a preferred inert support.

Catalysts comprising active elements which are advantageously at least 2 in number, one of which is copper, are preferred. Among the active elements other than copper, mention may be made of alkali metals, alkaline-earth metals, rare-earth metals and metals from the group composed of ruthenium, rhodium, palladium, osmium, iridium, platinum and gold. The catalysts containing the following active elements are particularly advantageous: copper/magnesium/potassium, copper/magnesium/sodium, copper/magnesium/lithium, copper/magnesium/caesium, copper/magnesium/sodium/lithium, copper/magnesium/potassium/lithium and copper/magnesium/caesium/lithium, copper/magnesium/sodium/potassium, copper/magnesium/sodium/caesium and copper/magnesium/potassium/caesium. The catalysts described in Patent Applications EP-A 255 156, EP-A 494 474, EP-A-657 212 and EP-A 657 213, incorporated by reference, are most particularly preferred.

The copper content, calculated in metal form, is advantageously between 30 and 90 g/kg, preferably between 40 and 80 g/kg and particularly preferably between 50 and 70 g/kg of the catalyst.

The magnesium content, calculated in metal form, is advantageously between 10 and 30 g/kg, preferably between 12 and 25 g/kg and particularly preferably between 15 and 20 g/kg of the catalyst.

The alkali metal content, calculated in metal form, is advantageously between 0.1 and 30 g/kg, preferably between 0.5 and 20 g/kg and particularly preferably between 1 and 15 g/kg of the catalyst.

The Cu/Mg/alkali metal(s) atomic ratios are advantageously 1/0.1-2/0.05-2, preferably 1/0.2-1.5/0.1-1.5 and particularly preferably 1/0.5-1/0.15-1.

Catalysts having a specific surface area measured according to the BET method with nitrogen advantageously comprised between 25 $m^2/g$ and 300 $m^2/g$, preferably between 50 and 200 $m^2/g$ and particularly preferably between 75 and 175 $m^2/g$, are particularly advantageous.

The catalysts may be used in a fixed bed or in a fluidized bed. This second option is preferred. The oxychlorination process is operated under the range of conditions usually recommended for this reaction. The temperature is advantageously between 150 and 300° C., preferably between 200 and 275° C. and most preferably from 215 to 255° C. The pressure is advantageously greater than atmospheric pressure. Values between 2 and 10 bar absolute have given good results. The range between 4 and 7 bar absolute is preferred. This pressure may usefully be adjusted to attain an optimum residence time in the reactor and to keep a constant rate of passage for various speeds of operation. The usual residence times range from 1 to 60 s and preferably from 10 to 40 s.

The source of oxygen for this oxychlorination may be air, pure oxygen or a mixture thereof, preferably pure oxygen. The latter solution, which allows easy recycling of the unconverted reactants, is preferred.

The reactants may be introduced into the bed by any known device. It is generally advantageous to introduce the oxygen separately from the other reactants for safety reasons. These safety reasons also require keeping the gas mixture leaving the reactor or recycled thereto outside the limits of inflammability at the pressures and temperatures in question. It is preferable to maintain a so-called rich mixture, that is to say containing too little oxygen relative to the fuel to ignite. In this regard, the abundant presence (>2 vol %, preferably >5 vol %) of hydrogen would constitute a disadvantage given the wide inflammability range of this compound.

The hydrogen chloride/oxygen ratio used is advantageously between 3 and 6 mol/mol. The ethylene/hydrogen chloride ratio is advantageously between 0.4 and 0.6 mol/mol.

The chlorinated products obtained mainly contain DCE and also small amounts of by-products such as 1,1,2-trichloroethane.

In certain cases, it may be advantageous, before entering into the oxychlorination reactor, to subject the stream of products derived from the chlorination reactor, from which the DCE has optionally been extracted, to the absorption/desorption step e'), during which the 1,2-dichloroethane formed in the chlorination reactor is optionally extracted if it has not previously been extracted.

The expression "step e'), during which the DCE formed in the chlorination reactor is optionally extracted if it has not previously been extracted" is understood to mean that the DCE formed in the chlorination reactor may be extracted during step e') if this step takes place and if it has not previously been extracted. Preferably, the DCE formed in the chlorination reactor is extracted during step e') if this step takes place and if it has not previously been extracted.

Step e') advantageously takes place in the case of the first variant of the process according to the invention according to which ODH takes place at temperatures greater than 650° C. up to 800° C. and the hydrogen content in the stream of products derived from the chlorination reactor is too high.

Thus, the stream of products derived from the chlorination reactor, from which the 1,2-dichloroethane has optionally been extracted, (known hereinafter as chlorination stream) is advantageously subjected to an absorption step and to a desorption step in which said stream is preferably brought into contact with a washing agent containing DCE.

The expression "washing agent containing DCE" or more simply "washing agent" is understood to mean a composition in which the DCE is present in the liquid state.

The washing agent that can be used according to the present invention therefore advantageously contains DCE in the liquid state. The presence, in said washing agent, of other compounds is not at all excluded from the scope of the invention. However, it is preferred that the washing agent contain at least 50 vol % of DCE, more particularly at least 80 vol % and most particularly preferably at least 95 vol %.

The washing agent used for the absorption step may be composed of fresh washing agent of any origin, for example crude DCE exiting the chlorination unit, crude DCE exiting the oxychlorination unit or a mixture of the two which has not been purified. It may also be composed of said DCE that has been previously purified or all or part of the washing agent recovered during the desorption step explained below optionally containing the DCE formed in the chlorination reactor and extracted in the desorption step, after an optional treatment making it possible to reduce the concentration, in the DCE, of the compounds that are heavier than ethane, as explained below, optionally with the addition of fresh washing agent.

Preferably, the washing agent used for the absorption step is composed of all or part of the washing agent recovered during the desorption step optionally containing the DCE formed in the chlorination reactor and extracted in the desorption step, after the abovementioned optional treatment, optionally with the addition of fresh washing agent. In the case where the DCE formed in the chlorination reaction is isolated from the stream of products derived from the chlorination reactor at the chlorination outlet, in a particularly preferred manner, the washing agent used for the absorption step is composed of all or part of the washing agent recovered during the desorption step, after the aforementioned optional treatment, with the addition of fresh washing agent (to compensate for losses of washing agent during the absorption and desorption steps).

The abovementioned optional treatment making it possible to reduce the concentration, in the washing agent, of the compounds that are heavier than ethane, preferably of the compounds comprising at least 3 carbon atoms, may be a step of desorbing the compounds that are heavier than ethane and lighter than the washing agent or a step of distilling the washing agent. Preferably, it consists of desorbing the compounds that are heavier than ethane and lighter than the washing agent. Preferably, this treatment of the washing agent takes place.

An essential advantage lies in the fact that the presence of this DCE is not at all troublesome, as it is the compound mainly formed during the oxychlorination or chlorination.

The ratio between the respective throughputs of washing agent and the chlorination stream is not critical and can vary to a large extent. It is in practice limited only by the cost of regenerating the washing agent. In general, the throughput of washing agent is at least 1, preferably at least 5 and particularly preferably at least 10 tonnes per tonne of chlorination stream. In general, the throughput of washing agent is at most 100, preferably at most 50 and particularly preferably at most 25 tonnes per tonne of the ethylene and ethane mixture to be extracted from the chlorination stream.

The absorption step is advantageously carried out by means of an absorber such as, for example, a climbing film or falling film absorber or an absorption column chosen from plate columns, columns with random packing, columns with structured packing, columns combining one or more of the aforementioned internals and spray columns. The absorption step is preferably carried out by means of an absorption column and particularly preferably by means of a plate absorption column.

The absorption column is advantageously equipped with associated accessories such as, for example, at least one condenser or chiller that is internal or external to the column.

The abovementioned absorption step is advantageously carried out at a pressure of at least 15, preferably of at least 20 and particularly preferably of at least 25 bar absolute. The absorption step is advantageously carried out at a pressure of at most 40, preferably at most 35 and particularly preferably at most 30 bar absolute.

The temperature at which the absorption step is carried out is advantageously at least −10, preferably at least 0 and particularly preferably at least 10° C. at the top of the absorber or absorption column. It is advantageously at most 60, preferably at most 50 and particularly preferably at most 40° C. at the top of the absorber or absorption column.

The temperature at the bottom of the absorber or absorption column is at least 0, preferably at least 10 and particularly preferably at least 20° C. It is advantageously at most 70, preferably at most 60 and particularly preferably at most 50° C.

The stream resulting from the absorption step, which is the chlorination stream purified of compounds that are lighter than ethylene, is advantageously subjected to the desorption step.

The washing agent recovered after the desorption step optionally containing the DCE formed in the chlorination reactor then extracted may be removed, completely or partly conveyed to the oxychlorination sector where the DCE comes together with the DCE formed in the oxychlorination reactor, or completely or partly reconveyed to the absorption step, optionally after the abovementioned treatment, with the optional addition of fresh washing agent. Preferably, the washing agent recovered after the desorption step is completely or partly reconveyed to the absorption step, after the abovementioned optional treatment, with optional addition of fresh washing agent, or to the oxychlorination sector. In the case where the DCE formed in the chlorination reactor is isolated from the stream of products derived from the chlorination reactor at the chlorination outlet, in a particularly preferred manner, the washing agent recovered after the desorption step is completely or partly reconveyed to the absorption step, after the abovementioned optional treatment, with addition of fresh washing agent.

The desorption step is advantageously carried out by means of a desorber such as, for example, a climbing film or falling film desorber, a reboiler or a desorption column chosen from plate columns, columns with random packing, columns with structured packing, columns combining one or more of the aforementioned internals and spray columns. The desorption step is preferably carried out by means of a desorption column and particularly preferably by means of a plate desorption column.

The desorption column is advantageously equipped with associated accessories such as, for example, at least one condenser or one chiller that is internal or external to the column and at least one reboiler.

The desorption pressure is advantageously chosen so that the content of compounds having at least 3 carbon atoms in the desorbed gas is less than 100 ppm, preferably less than or equal to 50 ppm and particularly preferably less than or equal to 20 ppm by volume.

The abovementioned desorption step is advantageously carried out at a pressure of at least 1, preferably at least 2 and particularly preferably at least 3 bar absolute. The desorption step is advantageously carried out at a pressure of at most 20, preferably at most 15 and particularly preferably at most 10 bar absolute.

The temperature at which the desorption step is carried out is advantageously at least −10, preferably at least 0 and particularly preferably at least 10° C. at the top of the desorber or desorption column. It is advantageously at most 60, preferably at most 50 and particularly preferably at most 45° C. at the top of the desorber or desorption column.

The temperature at the bottom of the desorber or desorption column is at least 60, preferably at least 80 and particularly preferably at least 100° C. It is advantageously at most 200, preferably at most 160 and particularly preferably at most 150° C.

A most particular preference is attached to the case where the absorption step is carried out in an absorption column and the desorption step in a desorption column.

The hydrogen recovered following the absorption step is advantageously developed as a fuel or as a reactant, optionally after a purification step. Thus, the hydrogen may be developed as a fuel in the DCE pyrolysis step or in the ODH step a). It may also be developed as a reactant for a hydrogenation reaction for example.

According to step f) of the process according to the invention, the DCE formed in the oxychlorination reactor is isolated from the stream of products derived from the oxychlorination reactor and is optionally added to the DCE formed in the chlorination reactor.

The separation of the DCE obtained from the stream of products derived from the oxychlorination reactor is carried out according to known methods. It is preferably carried out first by condensation. The heat of the oxychlorination reactor is generally recovered in the vapour state which may be used for the separations or for any other use.

After exiting from the oxychlorination reactor, the stream of products derived from the reactor is also advantageously washed to recover the unconverted HCl. This washing operation is advantageously an alkaline washing step. It is preferably followed by a gas/liquid separation step which makes it possible to recover the DCE formed in liquid form and finally to dry the DCE. The gases optionally recycled to the ODH are dried by cooling.

The expression "is optionally added to the DCE formed in the chlorination reactor" is understood to mean that if the DCE formed in the chlorination reactor is isolated from the stream of products derived from this reactor, on exiting the chlorination reactor or after step e'), the DCE formed in the oxychlorination reactor may or may not be added thereto. Preferably, it is added thereto. If on the other hand, this first DCE is not isolated, the DCE isolated from the stream of products derived from the oxychlorination reactor is advantageously the only stream of DCE recovered.

According to optional step g) of the process according to the invention, the stream of products derived from the oxychlorination reactor, from which the DCE has been extracted, optionally containing an additional stream of ethane previously introduced into one of steps b) to f), is optionally recycled to step a) after having been optionally purged of gases and/or after an optional additional treatment in order to eliminate the chlorinated products contained therein.

The stream of products derived from the oxychlorination reactor, from which the DCE has been extracted, may be recycled to step a) or not, during optional step g). Preferably, the stream of products derived from the oxychlorination reactor, from which the DCE has been extracted, is recycled to step a) during step g).

An additional stream of ethane introduced previously into one of steps b) to f) may therefore be found in this stream recycled at step g).

Thus, in the particular case where only a lean ethane stream, for example having 30 or 40 vol % of ethane, is available, it is advantageous to introduce this stream not into step a) directly but, for example, into the absorption/desorption step e') so that the light gases are extracted therefrom and the residual stream is recycled to the ODH during step g).

Similarly, in the particular case where the stream of ethane available is rich in sulfur compounds, it may be advantageous to introduce this stream not into step a) directly but, for example, into step b) to remove these troublesome compounds therefrom; after having undergone steps c) to f), this stream of ethane is then recycled to the ODH during step g).

The stream of products derived from the oxychlorination reactor, from which the DCE has been extracted, is advantageously characterized by an ethane content that is greater than or equal to 5%, preferably greater than or equal to 15%, particularly preferably greater than or equal to 30% and more particularly preferably greater than or equal to 40% by volume relative to the total volume of said stream.

The stream of products derived from the oxychlorination reactor, from which the DCE has been extracted, is advantageously characterized by an ethane content that is less than or equal to 95%, preferably less than or equal to 90%, particularly preferably less than or equal to 85% and more particularly preferably less than or equal to 80% by volume relative to the total volume of said stream.

The stream of products derived from the oxychlorination reactor, from which the DCE has been extracted, is advantageously characterized by an ethylene content that is less than or equal to 10%, preferably less than or equal to 5% and particularly preferably less than or equal to 2% by volume relative to the total volume of said stream.

The stream of products derived from the oxychlorination reactor, from which the DCE has been extracted, is advantageously characterized by a hydrogen content that is less than or equal to 10%, preferably less than or equal to 5% and particularly preferably less than or equal to 2% by volume relative to the total volume of said stream.

The stream of products derived from the oxychlorination reactor, from which the DCE has been extracted, is advantageously characterized by a content of carbon monoxide, carbon dioxide and nitrogen that is less than or equal to 70%, preferably less than or equal to 60%, and particularly preferably less than or equal to 55% by volume relative to the total volume of said stream.

The stream of products derived from the oxychlorination reactor, from which the DCE has been extracted, is advantageously characterized by an oxygen content that is less than or equal to 10%, preferably less than or equal to 5% and particularly preferably less than or equal to 3% by volume relative to the total volume of said stream.

According to step g) of the preferred process according to the invention, the stream of products derived from the oxychlorination reactor, from which the DCE has been extracted, optionally containing an additional stream of ethane previously introduced into one of steps b) to f), is recycled to step a).

The recycling to step a) is in this case performed after an optional purge of gases and/or after an optional additional treatment in order to eliminate the chlorinated products (notably traces of DCE and/or of other chlorinated products such as ethylene chloride) contained in the considered stream of products. The additional treatment when it takes place, may be performed by using active carbon or an adsorbent.

Either the purge of gases or the additional treatment or both of them may be performed. More preferably, the stream of products is recycled to step a) without being purged of gases and without any additional treatment in order to eliminate the chlorinated products contained in.

Indeed, the recycling of this stream of products to the ODH step a) may be interesting to benefit from the favourable catalytic effect of the chlorinated products on the ODH reaction.

Within the scope of the present invention a process for the manufacture of DCE starting from a stream of ethane is particularly preferred, according to which:
a) the stream of ethane is subjected to a catalytic oxydehydrogenation at a temperature above 650° C. producing a gas mixture containing ethylene, unconverted ethane, water and secondary constituents;
b) said gas mixture is optionally washed and dried thus producing a dry gas mixture;
c) after an optional additional purification step, the dry gas mixture is then conveyed to a chlorination reactor supplied with a flow of chlorine so that at least 10% of the ethylene is converted to 1,2-dichloroethane;
d) the 1,2-dichloroethane formed in the chlorination reactor is isolated from the stream of products derived from the chlorination reactor;
e) the stream of products derived from the chlorination reactor, from which the 1,2-dichloroethane has been extracted, is conveyed to an oxychlorination reactor in which the majority of the balance of ethylene is converted to 1,2-dichloroethane, after having subjected the latter to an absorption/desorption step e').
f) the 1,2-dichloroethane formed in the oxychlorination reactor is isolated from the stream of products derived from the oxychlorination reactor and is optionally added to the 1,2-dichloroethane formed in the chlorination reactor;
g) the stream of products derived from the oxychlorination reactor, from which the 1,2-dichloroethane has been extracted, is recycled to step a).

Within the scope of the present invention a process for the manufacture of DCE starting from a stream of ethane is also particularly preferred, according to which:
a) the stream of ethane is subjected to a catalytic oxydehydrogenation at a temperature less than or equal to 650° C. producing a gas mixture containing ethylene, unconverted ethane, water and secondary constituents;
b) said gas mixture is optionally washed and dried thus producing a dry gas mixture;
c) after an optional additional purification step, the dry gas mixture is then conveyed to a chlorination reactor supplied with a flow of chlorine so that at least 10% of the ethylene is converted to 1,2-dichloroethane;
d) the 1,2-dichloroethane formed in the chlorination reactor is isolated from the stream of products derived from the chlorination reactor;
e) the stream of products derived from the chlorination reactor, from which the 1,2-dichloroethane has been extracted, is conveyed to an oxychlorination reactor in which the majority of the balance of ethylene is converted to 1,2-dichloroethane;
f) the 1,2-dichloroethane formed in the oxychlorination reactor is isolated from the stream of products derived from the oxychlorination reactor and is optionally added to the 1,2-dichloroethane formed in the chlorination reactor;
g) the stream of products derived from the oxychlorination reactor, from which the 1,2-dichloroethane has been extracted, is recycled to step a).

The DCE obtained by chlorination and by oxychlorination of ethylene may then be converted into VC.

The invention therefore also relates to a process for the manufacture of VC. To this effect, the invention relates to a process for the manufacture of VC characterized in that:
a) a stream of ethane is subjected to a catalytic oxydehydrogenation producing a gas mixture containing ethylene, unconverted ethane, water and secondary constituents;
b) said gas mixture is optionally washed and dried thus producing a dry gas mixture;
c) after an optional additional purification step, the dry gas mixture is then conveyed to a chlorination reactor supplied with a flow of chlorine so that at least 10% of the ethylene is converted to 1,2-dichloroethane;
d) the 1,2-dichloroethane formed in the chlorination reactor is optionally isolated from the stream of products derived from the chlorination reactor;
e) the stream of products derived from the chlorination reactor, from which the 1,2-dichloroethane has optionally been extracted, is conveyed to an oxychlorination reactor in which the majority of the balance of ethylene is converted to 1,2-dichloroethane, after optionally having subjected the latter to an absorption/desorption step e'), during which the 1,2-dichloroethane formed in the chlorination reactor is optionally extracted if it has not previously been extracted;
f) the 1,2-dichloroethane formed in the oxychlorination reactor is isolated from the stream of products derived from the oxychlorination reactor and is optionally added to the 1,2-dichloroethane formed in the chlorination reactor;
g) the stream of products derived from the oxychlorination reactor, from which the 1,2-dichloroethane has been extracted, optionally containing an additional stream of ethane previously introduced in one of steps b) to f), is optionally recycled to step a) after having been optionally purged of gases and/or after an optional additional treatment in order to eliminate the chlorinated products contained therein;
h) the 1,2-dichloroethane obtained is subjected to a pyrolysis thus producing VC.

The particular conditions and preferences defined for the process for the manufacture of DCE according to the invention apply to the process for the manufacture of VC according to the invention.

The conditions under which the pyrolysis may be carried out are known to a person skilled in the art. This pyrolysis is advantageously achieved by a reaction in the gas phase in a tube furnace. The usual pyrolysis temperatures extend between 400 and 600° C. with a preference for the range between 480° C. and 540° C. The residence time is advantageously between 1 and 60 seconds with a preference for the range of 5 to 25 seconds. The conversion rate of the DCE is advantageously limited to 45 to 75% in order to limit the formation of by-products and fouling of the furnace pipes. The following steps make it possible, using any known device, to collect the purified VC and the hydrogen chloride to be upgraded preferably in the oxychlorination. Following purification, the unconverted DCE is advantageously reconveyed to the pyrolysis furnace.

In addition, the invention also relates to a process for the manufacture of PVC. To this effect, the invention relates to a process for the manufacture of PVC characterized in that:
a) a stream of ethane is subjected to a catalytic oxydehydrogenation producing a gas mixture containing ethylene, unconverted ethane, water and secondary constituents;
b) said gas mixture is optionally washed and dried thus producing a dry gas mixture;
c) after an optional additional purification step, the dry gas mixture is then conveyed to a chlorination reactor supplied with a flow of chlorine so that at least 10% of the ethylene is converted to 1,2-dichloroethane;
d) the 1,2-dichloroethane formed in the chlorination reactor is optionally isolated from the stream of products derived from the chlorination reactor;
e) the stream of products derived from the chlorination reactor, from which the 1,2-dichloroethane has optionally been extracted, is conveyed to an oxychlorination reactor in which the majority of the balance of ethylene is converted to 1,2-dichloroethane, after optionally having subjected the latter to an absorption/desorption step e'), during which the 1,2-dichloroethane formed in the chlorination reactor is optionally extracted if it has not previously been extracted;

f) the 1,2-dichloroethane formed in the oxychlorination reactor is isolated from the stream of products derived from the oxychlorination reactor and is optionally added to the 1,2-dichloroethane formed in the chlorination reactor;

g) the stream of products derived from the oxychlorination reactor, from which the 1,2-dichloroethane has been extracted, optionally containing an additional stream of ethane previously introduced in one of steps b) to f), is optionally recycled to step a) after having been optionally purged of gases and/or after an optional additional treatment in order to eliminate the chlorinated products contained therein;

h) the 1,2-dichloroethane obtained is subjected to a pyrolysis thus producing VC; and i) the VC is polymerized to produce PVC.

The particular conditions and preferences defined for the process for the manufacture of DCE and the process for the manufacture of VC according to the invention apply to the process for the manufacture of PVC according to the invention.

The process for the manufacture of PVC may be a bulk, solution or aqueous dispersion polymerization process, preferably it is an aqueous dispersion polymerization process.

The expression "aqueous dispersion polymerization" is understood to mean radical polymerization in aqueous suspension and also radical polymerization in aqueous emulsion and polymerization in aqueous microsuspension.

The expression "radical polymerization in aqueous suspension" is understood to mean any radical polymerization process performed in aqueous medium in the presence of dispersants and oil-soluble radical initiators.

The expression "radical polymerization in aqueous emulsion" is understood to mean any radical polymerization process performed in aqueous medium in the presence of emulsifiers and water-soluble radical initiators.

The expression "polymerization in aqueous microsuspension", also called polymerization in homogenized aqueous dispersion, is understood to mean any radical polymerization process in which oil-soluble initiators are used and an emulsion of monomer droplets is prepared by virtue of a powerful mechanical stirring and the presence of emulsifiers.

In relation to a similarly simplified thermal cracking process, the process according to the invention making use of an ODH step has the advantage of combining an endothermic step (ethane converted into ethylene) with an exothermic water production step, of taking place at a moderate temperature and of avoiding having to provide the heat of reaction at a high temperature.

The process according to the invention also has the advantage of making it possible to recycle the stream of products derived from the oxychlorination, from which the DCE has been extracted, to the ODH step, thus ensuring an increased conversion of ethane into ethylene. Furthermore, given the moderate temperature of the ODH relative to thermal cracking, even if this recycled stream contains traces of chlorinated organic products such as DCE, their presence does not cause material behaviour and corrosion problems as occur in the case of thermal cracking above 800° C. The presence of chlorinated products may furthermore be advantageous in so far as it allows an increase of the efficiency of the ODH reaction.

The process according to the invention has the advantage of not generating compounds comprising at least 3 carbon atoms in troublesome amounts, these compounds generally being responsible for a certain inhibition during the pyrolysis of the DCE. This inhibition is due to the formation of derivatives such as 1,2-dichloropropane and monochloropropenes. Their aptitude for forming stable allyl radicals explains their powerful inhibitory effect on the pyrolysis of DCE which is carried out by the radical route. The formation of these by-products containing 3 carbon atoms and heavier by-products furthermore constitutes an unnecessary consumption of reactants in the oxychlorination and in the chlorination, or generates costs for destroying them. Furthermore, these heavy compounds contribute to the soiling of the columns and evaporators.

Since the ODH reaction takes place at a lower temperature than thermal cracking, the process according to the invention is advantageously characterized, in addition, by the fact that the formation of heavy compounds by oligomerization is much lower.

The process according to the invention making use of an ODH step also has the advantage of limiting the conversion by passing to the ODH without having to resort to expensive separations such as those that require an ethylene distillation.

Another advantage of the process according to the invention is that it makes it possible to have, on the same industrial site, a completely integrated process ranging from the hydrocarbon source—namely ethane—up to the polymer obtained starting from the monomer manufactured.

The second variant of the process according to the invention, according to which the ODH takes place at temperatures less than or equal to 650° C., has the advantage of generating very small amounts of hydrogen, responsible for numerous drawbacks.

The first variant of the process for the manufacture of DCE according to the invention will now be illustrated with reference to the drawing accompanying the present description. This drawing consists of the appended FIG. 1, schematically representing an embodiment of the process for the manufacture of DCE according to the invention.

A stream of ethane 1 and a source of oxygen 2 are introduced into the reactor 3 there to be subjected to an ODH at a temperature above 650° C. The gas mixture containing ethylene, unconverted ethane, water and secondary constituents 4 produced during the ODH step is subjected to washing and drying in 5 in order to remove by-products as well as water (6) therefrom. After an optional additional purification step, the dry gas mixture formed is then conveyed to a chlorination reactor 7 supplied with a flow of chlorine 8 so that at least 10% of the ethylene is converted to DCE. The DCE 11 formed in the chlorination reactor is separated in 10 from the stream of products 9 derived from the chlorination reactor. The stream of products 12 derived from the chlorination reactor from which the DCE has been extracted is then subjected to an absorption/desorption step 13 in order to eliminate the compounds which are lighter than ethylene, among which hydrogen (13bis), which may be valorised thermally, chemically or hydraulically, before being conveyed to an oxychlorination reactor 14, supplied with hydrogen chloride 15 and oxygen 16, in which the majority of the balance of ethylene is converted to DCE. The liquid DCE 19 formed in the oxychlorination reactor accompanied by liquefied by-products among which water, is isolated in 18 by condensation followed by washing and gas/liquid separation from the stream of products 17 derived from the oxychlorination reactor. The stream of products 20 derived from the oxychlorination reactor from which the DCE 19 has been extracted is finally recycled to the ODH step.

Figure 2:
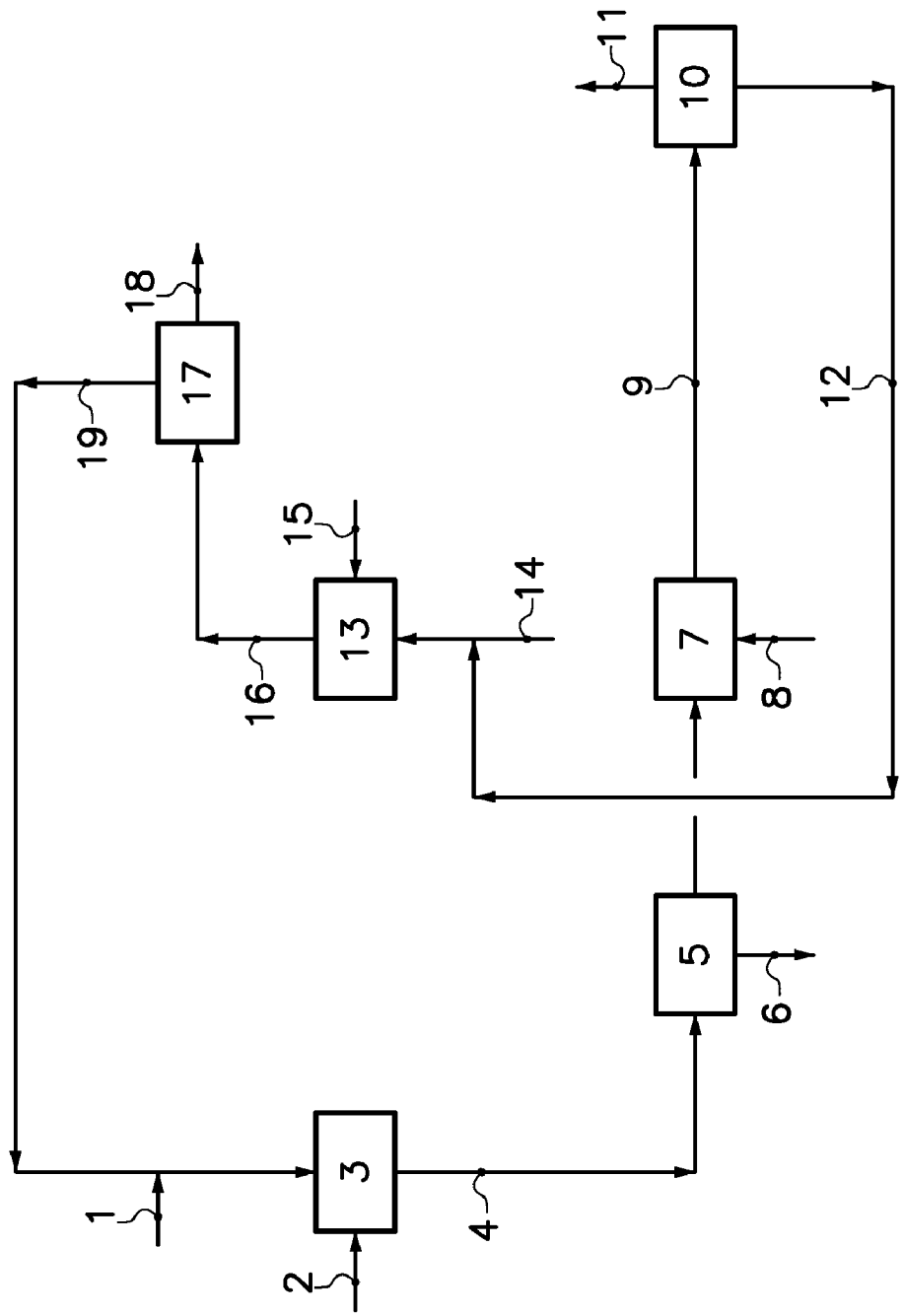
FIG. 2 illustrates a second embodiment of the process for the manufacture of DCE according to the invention.

The second preferred variant of the process for the manufacture of DCE according to the invention will now be illustrated with reference to the drawing accompanying the present description. This drawing consists of the appended FIG. 2, schematically representing an embodiment of the process for the manufacture of DCE according to the invention.

A stream of ethane 1 and a source of oxygen 2 are introduced into the reactor 3 there to be subjected to an ODH at a temperature less than or equal to 650° C. The gas mixture containing ethylene, unconverted ethane, water and secondary constituents 4 produced during the ODH step is subjected to washing and drying in 5 in order to remove by-products as well as water (6) therefrom. After an optional additional purification step, the dry gas mixture formed is then conveyed to a chlorination reactor 7 supplied with a flow of chlorine 8 so that at least 10% of the ethylene is converted to DCE. The DCE 11 formed in the chlorination reactor is separated in 10 from the stream of products 9 derived from the chlorination reactor. The stream of products 12 derived from the chlorination reactor from which the DCE has been extracted is then conveyed to an oxychlorination reactor 13, supplied with hydrogen chloride 14 and oxygen 15, in which the majority of the balance of ethylene is converted to DCE. The liquid DCE 18 formed in the oxychlorination reactor accompanied by liquefied by-products among which water, is isolated in 17 by condensation followed by washing and gas/liquid separation from the stream of products 16 derived from the oxychlorination reactor. The stream of products 19 derived from the oxychlorination reactor from which the DCE 18 has been extracted is finally recycled to the ODH step.

The invention claimed is:

1. A process for the manufacture of 1,2-dichloroethane starting from a stream of ethane, comprising:
    a) subjecting the stream of ethane to a catalytic oxydehydrogenation thus producing a gas mixture containing ethylene, unconverted ethane, water and secondary constituents;
    b) drying said gas mixture thus producing a dry gas mixture, wherein said gas mixture is optionally washed before or after said drying;
    c) after an optional additional purification step, conveying the dry gas mixture to a chlorination reactor supplied with a flow of chlorine so that at least 10% of the ethylene is converted to 1,2-dichloroethane;
    d) optionally isolating the 1,2-dichloroethane formed in the chlorination reactor from the stream of products derived from the chlorination reactor;
    e) conveying the stream of products derived from the chlorination reactor, from which the 1,2-dichloroethane has optionally been extracted in step d), to an oxychlorination reactor in which the majority of the balance of ethylene is converted to 1,2-dichloroethane, after optionally having subjected the latter to an absorption/desorption step e'), during which the 1,2-dichloroethane formed in the chlorination reactor is optionally extracted if it has not previously been extracted;
    f) isolating the 1,2-dichloroethane formed in the oxychlorination reactor from the stream of products derived from the oxychlorination reactor, wherein said 1,2-dichloroethane formed in the oxychlorination reactor is optionally added to the 1,2-dichloroethane formed in the chlorination reactor; and
    g) optionally recycling to step a) the stream of products derived from the oxychlorination reactor, from which the 1,2-dichloroethane has been extracted, optionally containing an additional stream of ethane previously introduced in one of steps b) to f), after having been optionally purged of gases and/or after an optional additional treatment in order to eliminate the chlorinated products contained therein.

2. The process according to claim 1, wherein the stream of ethane contains at least 80 vol % of ethane.

3. The process according to claim 1, wherein the stream of ethane contains at least 98 vol % of ethane.

4. The process according to claim 1, wherein the catalytic oxydehydrogenation from step a) takes place at a temperature less than or equal to 650° C.

5. The process according to claim 1, wherein during step b), said gas mixture is washed and dried, thus producing a dry gas mixture.

6. The process according to claim 1, wherein during step c), the flow of chlorine is such that at most 90% of the ethylene is converted to 1,2-dichloroethane.

7. The process according to claim 1, wherein during step c), the flow of chlorine is such that at least 40% of the ethylene is converted to 1,2-dichloroethane.

8. The process according to claim 1, comprising:
    a) subjecting the stream of ethane to a catalytic oxydehydrogenation at a temperature less than or equal to 650° C. thus producing a gas mixture containing ethylene, unconverted ethane, water and secondary constituents;
    b) drying said gas mixture thus producing a dry gas mixture, wherein said gas mixture is optionally washed before or after said drying;
    c) after an optional additional purification step, conveying the dry gas mixture to a chlorination reactor supplied with a flow of chlorine so that at least 10% of the ethylene is converted to 1,2-dichloroethane;
    d) isolating the 1,2-dichloroethane formed in the chlorination reactor from the stream of products derived from the chlorination reactor;
    e) conveying the stream of products derived from the chlorination reactor, from which the 1,2-dichloroethane has been extracted in step d), to an oxychlorination reactor in which the majority of the balance of ethylene is converted to 1,2-dichloroethane;
    f) isolating the 1,2-dichloroethane formed in the oxychlorination reactor from the stream of products derived from the oxychlorination reactor, wherein said 1,2-dichloroethane formed in the oxychlorination reactor is optionally added to the 1,2-dichloroethane formed in the chlorination reactor; and
    g) recycling to step a) the stream of products derived from the oxychlorination reactor, from which the 1,2-dichloroethane has been extracted.

9. A process for manufacturing vinyl chloride, comprising:
    a) subjecting the stream of ethane to a catalytic oxydehydrogenation thus producing a gas mixture containing ethylene, unconverted ethane, water and secondary constituents;
    b) drying said gas mixture thus producing a dry gas mixture, wherein said gas mixture is optionally washed before or after said drying;
    c) after an optional additional purification step, conveying the dry gas mixture to a chlorination reactor supplied with a flow of chlorine so that at least 10% of the ethylene is converted to 1,2-dichloroethane;
    d) optionally isolating the 1,2-dichloroethane formed in the chlorination reactor from the stream of products derived from the chlorination reactor;
    e) conveying the stream of products derived from the chlorination reactor, from which the 1,2-dichloroethane has optionally been extracted in step d), to an oxychlorination reactor in which the majority of the balance of ethylene is converted to 1,2-dichloroethane, after optionally having subjected the latter to an absorption/desorption step e'), during which the 1,2-dichloroethane formed in the chlorination reactor is optionally extracted if it has not previously been extracted;

f) isolating the 1,2-dichloroethane formed in the oxychlorination reactor from the stream of products derived from the oxychlorination reactor, wherein said 1,2-dichloroethane formed in the oxychlorination reactor is optionally added to the 1,2-dichloroethane formed in the chlorination reactor;

g) optionally recycling to step a) the stream of products derived from the oxychlorination reactor, from which the 1,2-dichloroethane has been extracted, optionally containing an additional stream of ethane previously introduced in one of steps b) to f), after having been optionally purged of gases and/or after an optional additional treatment in order to eliminate the chlorinated products contained therein; and h) subjecting the 1,2-dichloroethane so obtained to a pyrolysis thus producing vinyl chloride.

10. A process for the manufacture of polyvinyl chloride, comprising:

a) subjecting the stream of ethane to a catalytic oxydehydrogenation thus producing a gas mixture containing ethylene, unconverted ethane, water and secondary constituents;

b) drying said gas mixture thus producing a dry gas mixture, wherein said gas mixture is optionally washed before or after said drying;

c) after an optional additional purification step, conveying the dry gas mixture to a flow of chlorine so that at least 10% of the ethylene is converted to 1,2-dichloroethane;

d) optionally isolating the 1,2-dichloroethane formed in the chlorination reactor from the stream of products derived from the chlorination reactor;

e) conveying the stream of products derived from the chlorination reactor, from which the 1,2-dichloroethane has optionally been extracted in step d), to an oxychlorination reactor in which the majority of the balance of ethylene is converted to 1,2-dichloroethane, after optionally having subjected the latter to an absorption/desorption step e'), during which the 1,2-dichloroethane formed in the chlorination reactor is optionally extracted if it has not previously been extracted;

f) isolating the 1,2-dichloroethane formed in the oxychlorination reactor from the stream of products derived from the oxychlorination reactor and is optionally added to the 1,2-dichloroethane formed in the chlorination reactor;

g) optionally recycling to step a) the stream of products derived from the oxychlorination reactor, from which the 1,2-dichloroethane has been extracted, optionally containing an additional stream of ethane previously introduced in one of steps b) to f), after having optionally being purged of gases and/or after an optional additional treatment in order to eliminate the chlorinated products contained therein;

h) subjecting the 1,2-dichloroethane obtained to a pyrolysis thus producing vinyl chloride; and i) polymerizing the vinyl chloride to produce polyvinyl chloride.

11. The process according to claim 1, wherein mixed oxides containing both Mo and V; W and V or Mo; or W and V are used as a catalytic system to carry out the catalytic oxydehydrogenation.

12. The process according to claim 11, according to which the mixed oxides are selected from the group consisting of Mo—W—V—Ta—Te—Ti—P—Ni—Ce—O, Mo—W—V—Ta—Te—Ti—P—O, Mo—W—V—Te—Ti—P—Ce—O, Mo—W—V—Te—Ti—P—Ni—O, Mo—W—V—Te—Ti—P—O, Mo—W—V—Te—Ti—O, Mo—W—V—Te—P—O, Mo—W—V—Te—O, Mo—W—V—Ta—Te—Ti—P—Ni—Ce—O, Mo—W—V—Ta—Te—Ti—P—O, Mo—W—V—Te—Ti—P—Ce—O, Mo—W—V—Te—Ti—P—Ni—O, Mo—W—V—Te—Ti—P—O, Mo—W—V—Te—Ti—O, Mo—W—V—Te—P—O, Mo—W—V—Te—O, Mo—W—V—Nb—O, Mo—W—V—Sb—O, Mo—W—V—Ti—Sb—Bi—O, Mo—W—V—Ti—Sb—O, Mo—W—V—Sb—Bi—O, Mo—W—V—Zr—O, Mo—W—V—Nb—Ta—O, Mo—W—V—Nb—O, and Mo—W—V—O.

13. The process according to claim 9, wherein during step b), said gas mixture is washed and dried, thus producing a dry gas mixture.

14. The process according to claim 9, wherein during step c), the flow of chlorine is such that at most 90% of the ethylene is converted to 1,2-dichloroethane.

15. The process according to claim 9, wherein during step c), the flow of chlorine is such that at least 40% of the ethylene is converted to 1,2-dichloroethane.

16. The process according to claim 9, wherein mixed oxides containing both Mo and V; W and V or Mo; or W and V are used as a catalytic system to carry out the catalytic oxydehydrogenation.

17. The process according to claim 16, according to which the mixed oxides are selected from the group consisting of Mo—W—V—Ta—Te—Ti—P—Ni—Ce—O, Mo—W—V—Ta—Te—Ti—P—O, Mo—W—V—Te—Ti—P—Ce—O, Mo—W—V—Te—Ti—P—Ni—O, Mo—W—V—Te—Ti—P—O, Mo—W—V—Te—Ti—O, Mo—W—V—Te—P—O, Mo—W—V—Te—O, Mo—W—V—Ta—Te—Ti—P—Ni—Ce—O, Mo—W—V—Ta—Te—Ti—P—O, Mo—W—V—Te—Ti—P—Ce—O, Mo—W—V—Te—Ti—P—Ni—O, Mo—W—V—Te—Ti—P—O, Mo—W—V—Te—Ti—O, Mo—W—V—Te—P—O, Mo—W—V—Te—O, Mo—W—V—Nb—O, Mo—W—V—Sb—O, Mo—W—V—Ti—Sb—Bi—O, Mo—W—V—Ti—Sb—O, Mo—W—V—Sb—Bi—O, Mo—W—V—Zr—O, Mo—W—V—Nb—Ta—O, Mo—W—V—Nb—O, and Mo—W—V—O.

18. The process according to claim 10, wherein during step b), said gas mixture is washed and dried, thus producing a dry gas mixture.

19. The process according to claim 10, wherein during step c), the flow of chlorine is such that at most 90% of the ethylene is converted to 1,2-dichloroethane.

20. The process according to claim 10, wherein during step c), the flow of chlorine is such that at least 40% of the ethylene is converted to 1,2-dichloroethane.

21. The process according to claim 10, wherein mixed oxides containing both Mo and V; W and V or Mo; or W and V are used as a catalytic system to carry out the catalytic oxydehydrogenation.

22. The process according to claim 21, according to which the mixed oxides are selected from the group consisting of Mo—W—V—Ta—Te—Ti—P—Ni—Ce—O, Mo—W—V—Ta—Te—Ti—P—O, Mo—W—V—Te—Ti—P—Ce—O, Mo—W—V—Te—Ti—P—Ni—O, Mo—W—V—Te—Ti—P—O, Mo—W—V—Te—Ti—O, Mo—W—V—Te—P—O, Mo—W—V—Te—O, Mo—W—V—Ta—Te—Ti—P—Ni—Ce—O, Mo—W—V—Ta—Te—Ti—P—O, Mo—W—V—Te—Ti—P—Ce—O, Mo—W—V—Te—Ti—P—Ni—O, Mo—W—V—Te—Ti—P—O, Mo—W—V—Te—Ti—O, Mo—W—V—Te—P—O, Mo—W—V—Te—O, Mo—W—V—Nb—O, Mo—W—V—Sb—O, Mo—W—V—Ti—Sb—Bi—O, Mo—W—V—Ti—Sb—O, Mo—W—V—Sb—Bi—O, Mo—W—V—Zr—O, Mo—W—V—Nb—Ta—O, Mo—W—V—Nb—O, and Mo—W—V—O.

* * * * *